United States Patent
Davidian et al.

(10) Patent No.: US 9,694,345 B2
(45) Date of Patent: Jul. 4, 2017

(54) CATALYST COMPOSITION FOR THE SELECTIVE CONVERSION OF SYNTHESIS GAS TO LIGHT OLEFINS

(71) Applicant: Dow Global Technologies LLC, Midland, MI (US)

(72) Inventors: Thomas Davidian, Ghent (BE); Matthijs Ruitenbeek, Terneuzen (NL); Adam Chojecki, Ghent (BE); Adrianus Koeken, Terneuzen (NL)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/889,483

(22) PCT Filed: Jun. 25, 2014

(86) PCT No.: PCT/US2014/043985
§ 371 (c)(1),
(2) Date: Nov. 6, 2015

(87) PCT Pub. No.: WO2014/210090
PCT Pub. Date: Dec. 31, 2014

(65) Prior Publication Data
US 2016/0107144 A1    Apr. 21, 2016

Related U.S. Application Data

(60) Provisional application No. 61/840,650, filed on Jun. 28, 2013.

(51) Int. Cl.
| | |
|---|---|
| C07C 1/04 | (2006.01) |
| B01J 21/06 | (2006.01) |
| B01J 23/02 | (2006.01) |
| B01J 23/04 | (2006.01) |
| B01J 23/10 | (2006.01) |
| B01J 23/745 | (2006.01) |
| B01J 23/76 | (2006.01) |
| B01J 23/83 | (2006.01) |
| B01J 27/053 | (2006.01) |
| B01J 27/22 | (2006.01) |
| B01J 37/02 | (2006.01) |
| B01J 37/08 | (2006.01) |
| B01J 23/78 | (2006.01) |

(52) U.S. Cl.
CPC .......... *B01J 23/10* (2013.01); *B01J 21/066* (2013.01); *B01J 23/745* (2013.01); *B01J 23/78* (2013.01); *B01J 23/83* (2013.01); *B01J 27/22* (2013.01); *B01J 37/0205* (2013.01); *C07C 1/044* (2013.01); *B01J 37/084* (2013.01); *C07C 2521/06* (2013.01); *C07C 2523/04* (2013.01); *C07C 2523/10* (2013.01); *C07C 2523/745* (2013.01); *C07C 2523/78* (2013.01); *C07C 2523/83* (2013.01); *C07C 2527/224* (2013.01); *Y02P 20/52* (2015.11)

(58) Field of Classification Search
CPC ... B01J 23/02; B01J 23/04; B01J 23/10; B01J 23/745; B01J 23/78; B01J 23/83; B01J 21/066; B01J 37/0205; B01J 37/08; B01J 37/084; B01J 27/053; B01J 27/22; C07C 1/044
USPC ....... 502/302, 327, 328, 330, 332, 336, 338, 502/349, 355
See application file for complete search history.

(56) References Cited

U.S. PATENT DOCUMENTS

| | | | | |
|---|---|---|---|---|
| 5,075,277 A | * | 12/1991 | Saiai | B01J 23/10 502/332 |
| 8,003,565 B2 | * | 8/2011 | Hagemeyer | B01J 23/40 502/240 |
| 2014/0024727 A1 | | 1/2014 | de Jong et al. | |

FOREIGN PATENT DOCUMENTS

| | | |
|---|---|---|
| EP | 2314557 A1 | 4/2011 |
| WO | 03042263 A2 | 5/2003 |
| WO | 2008009076 A2 | 1/2008 |
| WO | 2009002222 A2 | 12/2008 |
| WO | 2012138415 A1 | 10/2012 |

OTHER PUBLICATIONS

Bian et al., "Studies with a precipitated iron Fischer-Tropsch catalyst reduced by H2 or CO", Journal of Molecular catalysis A: Chemical 186, pp. 203-213, Apr. 2002.
Chen et al., "Carbon monoxide hydrogenation on Fe2O3/ZrO2 catalysts", Catalysis Letters 36, pp. 139-144, 1996.
Chen et al., "CO hydrogenation over zirconia supported iron catalysts promoted with rare earth oxides", Applied Catalysis A: General 158, pp. 215-223, 1997.
Indarto et al., "Partial Oxidation of Methane with Sol-Gel Fe/Hf/ YSZ Catalyst in Dielectric Barrier Discharge: Catalyst Activation by Plasma", Journal of Rare Earths 24, pp. 513-518, 2006.
Luo et al, "Fischer-Tropsch Synthesis Catalyst activation of low alpha iron catalyst", Catalysis Today 140, pp. 127-134, 2009.
Shroff et al., "Activation of Precipitated Iron Fischer-Tropsch Synthesis Catalysts", Journal of Catalysis 156, pp. 185-207, 1995.
Search Report & Written Opinion for Application No. PCT/US2014/043985 dated Oct. 9, 2014.
International Preliminary Report on Patentability for Application No. PCT/2014/043985 dated Sep. 25, 2015.
European Communication for Application No. 14741476.7 dated Feb. 10, 2016.

\* cited by examiner

*Primary Examiner* — Cam N. Nguyen
(74) *Attorney, Agent, or Firm* — Dinsmore & Shohl LLP

(57) ABSTRACT

A catalyst composition and process for preparing it and for using it to enhance the selectivity to light (C2 to C3) olefins in a Fischer-Tropsch conversion of synthesis gas is disclosed. The catalyst composition is an iron-based catalyst on an yttria/zirconia support. In a Fischer-Tropsch reaction the selectivity to ethylene may be enhanced by at least 20 mole percent and to propylene by at least 4 mole percent, in comparison with use of an otherwise identical catalyst that is free of yttria, in an otherwise identical Fischer-Tropsch reaction.

14 Claims, No Drawings

CATALYST COMPOSITION FOR THE SELECTIVE CONVERSION OF SYNTHESIS GAS TO LIGHT OLEFINS

CROSS-REFERENCE TO A RELATED APPLICATION

The present application claims priority to U.S. Patent Application Ser. No. 61/840,650, filed Jun. 28, 2013, which is incorporated herein by reference in its entirety.

The present invention relates to the field of conversion of synthesis gas to hydrocarbons. More particularly, the present invention relates to a catalyst composition that enhances selectivity to C2-C3 olefins in such conversions.

Synthesis gas has been used as a feedstock for many years as a non-petroleum source to prepare a variety of hydrocarbon products. These products are then, in many cases, used as starting materials for plastics, lubricants, fuels, and other widely-employed applications.

Generally synthesis gas is converted to liquid hydrocarbons via the well-known Fischer-Tropsch (FT) process. In this process a catalyst is used at a temperature ranging from, in many cases, 200° C. to 300° C. ("Low Temperature Fischer-Tropsch," LTFT, processes), or for higher temperature processes, frequently from 300° C. to 350° C. ("High Temperature Fischer-Tropsch," HTFT, processes). The catalysts commonly include transition metals such as cobalt, iron, nickel or ruthenium. Of these, cobalt-based catalysts may exhibit better activity, but iron may be preferred for low-hydrogen content synthesis gases, and each type of catalyst may be preferred for other reasons as well. Supported, high surface-area catalysts are frequently employed, with supports including, in many instances, silica, alumina or zeolites.

It is generally understood that in cobalt-based or ruthenium-based catalysts, the metal usually remains in its metallic state, while in iron-based catalysts, the iron must generally be present in specific phases in order for the catalyst to exhibit acceptable or desired levels of activity for specific processes.

Promoter selection is also important and may strongly influence catalytic activity. Alkali metals frequently operate well with iron-based catalysts, and reduce activity of cobalt-based catalysts. A particular and often undesirable effect of combining alkali metals with cobalt-based catalysts is that such combinations tend to exhibit increased selectivity to C5+ compounds and $CO_2$, while at the same time selectivity to methane and C2-C4 compounds is decreased. Researchers have sought ways and means to alter selectivity and identify catalysts offering the most desirable product mixes.

For example, WO 20030402263 A2 discloses a modified zirconia support for a cobalt-based FT catalyst. The catalyst shows up to 70% improvement in the FT reaction as compared to a corresponding catalyst supported on unmodified zirconia. The modifications include silica-zirconia, sulfated-zirconia and tungstated zirconia. While applied in the LTFT reaction, i.e. at temperatures well below 300° C., pressures up to 3 MPa, and $H_2$:CO ratio greater than 1.5, the improved performance relates to the increased yield to C11+ products and a lower ratio of olefins to paraffins. No improvement towards lights olefins is reported.

K. Chen, et al., "Carbon monoxide hydrogenation on $Fe_2O_3/ZrO_2$ catalysts," *Catal. Letters* 36 (1996) 139-144, discusses $Fe_2O_3/ZrO_2$ catalysts prepared by impregnation and co-precipitation methods used for catalytic hydrogenation of CO. It is shown that the structure, reduction behavior of the iron species, and catalytic properties of the catalysts are affected by preparation methods. For the $Fe_2O_3/ZrO_2$ catalyst prepared by the impregnation method, the HTFT catalytic activity and the selectivity to light olefins is much higher than for equivalent catalysts prepared by co-precipitation. At the same time the formation of methane is suppressed.

In another article by Chen et al., "CO hydrogenation over zirconia supported iron catalysts promoted with rare earth oxides", *Applied Catalysis A: General* 158 (1997), 215-223, it is reported that addition of ceria ($CeO_2$), or lanthania ($La_2O_3$) has benefits. For the $Fe/La/ZrO_2$ sample, the catalytic activity slightly higher than that of the $Fe/ZrO_2$ sample, but light olefins selectivity increases and methane formation is suppressed. For the $Fe/Ce/ZrO_2$ sample, the catalytic activity is much higher than that of the $Fe/ZrO_2$ sample, while methane formation is at significant levels and light olefins selectivity slightly increases.

Despite the advances in this field, there is still a need for new catalytic compositions that exhibit desirable activity levels and enhanced selectivity toward desirable products.

In one aspect the invention provides a catalyst for use in converting synthesis gas into olefins, comprising iron, and optionally, an alkali metal, alkaline earth metal or a combination thereof, on a support comprising zirconia and yttria, the iron being present in an amount ranging from 1 weight percent to 20 weight percent, based on combined weight of the iron and the support; the yttria being present in an amount ranging from 1 mole percent to 95 mole percent, based on combined moles of yttria and zirconia, and the optional alkali metal, alkaline earth metal or combination thereof being present in an amount ranging from 0 mole percent to 6 mole percent, based on moles of the iron.

In another aspect the invention provides a process for converting synthesis gas to olefins, comprising contacting synthesis gas and the catalyst as described hereinabove, under reaction conditions sufficient to convert, at a selected carbon monoxide conversion percent, at least a portion of the synthesis gas to a mixture of hydrocarbons that has an ethylene content and a propylene content, each of the ethylene content and the propylene content being greater than the ethylene content and the propylene content resulting from use of an otherwise identical catalyst that is substantially free of yttria, under identical reaction conditions and at a carbon monoxide conversion percent that is within 2 percent of the selected carbon monoxide conversion percent.

In still another aspect the invention provides a catalyst for use in converting synthesis gas to olefins, prepared by a process comprising (1) dispersing an iron-containing compound and, optionally, an alkali metal, an alkaline earth metal, or a combination thereof, on a particulate catalyst support comprising zirconia and yttria; the amount of the iron-containing compound ranging from 1 weight percent to 20 weight percent, based on combined weight of the iron and the support; the amount of the optional alkali metal, alkaline earth metal, or combination thereof ranging from 0 mole percent to 6 mole percent, based on combined moles of the alkali metal, the alkaline earth metal, or combination thereof and the iron; and the amount of yttria ranging from 0.1 mole percent to 95 mole percent, based on combined moles of yttria and zirconia; (2) thermally at least partially decomposing the iron-containing compound to form a catalyst precursor composition comprising an iron oxide; (3) subjecting the catalyst precursor composition to at least partial carburization in a carbon monoxide-containing atmosphere to convert at least some of the iron oxides to iron carbides.

The invention provides a catalyst, a process for making it, and a process for using it for a FT conversion of synthesis gas to light olefins, and more particularly with increased ethylene/ethane and propylene/propane ratios. By enhancing selectivity of light olefin content in a typical FT synthesis reaction, the separation of such olefins and any paraffins also produced is made easier to accomplish and less energy-intensive, and therefore, also less expensive.

The catalyst is formed from a catalyst precursor composition, which is generally defined as including iron, yttrium, and zirconium. The iron may be initially obtained from a variety of iron-containing compounds, through different preparation methods. Examples of iron-containing compounds are inorganic and organic iron salts, iron chelates, iron clusters, iron hydroxides and oxyhydroxides, and iron organometallic complexes. Non-limiting representatives of these compounds may include, for example, iron tetracarbonyl, iron pentacarbonyl, iron nonacarbonyl, iron nitrates, bromides, chlorides, fluorides, phosphates, sulfates, acetylacetonates, acetates, fumarates, gluconates, citrates, benzoates, maleates, oxalates, oleates, stearates, and the like. Thus, the iron-containing compound may provide iron to the catalyst precursor composition in a ferrous form, a ferric form, or a combination thereof. In particular embodiments the starting iron-containing compound preferably comprises Fe(II) or Fe(III) in combination with organic ligands or anions such as acetate, citrate, EDTA (ethylene diamine tetra acetate) or NTA (nitrilo triacetate) and, in certain embodiments, may include iron(II) carboxylate compounds, e.g., hydroxy-carboxylic iron compounds including ammonium, sodium or potassium salts, and ammonium iron citrate. One particularly convenient form of iron-containing starting compound may be ammonium iron(III) citrate.

Zirconia may be conveniently obtained from a variety of commercial sources. Alternatively, zirconia may be obtained from a wide variety of zirconium salts, such as, in non-limiting example, silicates, chlorides, carbides, nitrides, nitrates, carbonates, and so forth. Those skilled in the art will be aware of routes to convert such starting materials to the oxide form, e.g., $ZrO_2$.

Similarly, it may be most convenient and/or economical to obtain yttria from a commercial source, but it may alternatively be prepared via known reactions from starting materials such as yttrium halides, hydrides, nitrates, sulfates, and the like. $Y_2O_3$ is frequently the most convenient form. Without wishing to be bound by any theory, it is conjectured that one of the roles of the yttria may be to provide mechanical strength to the zirconia crystal structure, possibly by replacement of certain atoms in the crystal lattice of the zirconia.

While the invention is operable provided adequate amounts of each of the above-identified materials is included in the form of a supported catalyst precursor composition, in particularly preferred embodiments the final catalyst is characterized by its relatively high level of yttria which, in combination with the iron-containing starting material and the zirconia present in the support, forms a surprisingly active catalyst precursor composition that in particular embodiments shows significant selectivity to olefins.

In preparing this particular embodiment of the catalyst precursor composition, a preferably porous zirconia support that includes, preferably uniformly dispersed throughout, the yttria component may be prepared using means and methods generally known to those skilled in the art. For example, zirconia and yttria precursors, e.g., the salts as identified hereinabove, may be first co-precipitated and then converted, via drying and calcining in air or in an oxygen-containing atmosphere, to form a mixed zirconia-yttria support. Alternatively, solid particles comprising a mixture of zirconia and yttria may be mixed and fused in an oxygen-containing atmosphere. Those skilled in the art will be aware of additional means and methods for preparing the porous support material.

Following formation of the support as described hereinabove, the selected iron-containing compound may then be dispersed via a suitable method, such as, for example only, wet impregnation, chemical vapor deposition, or incipient wetness impregnation, onto the support. The support material that now includes, deposited on or in it, the iron-containing compound may then be heat-treated or calcined, at a temperature of at least 200° C. and preferably from 300° C. to 600° C., preferably from 450° C. to 550° C., to yield a catalyst precursor composition that comprises iron oxide species, as well as the zirconia and yttria.

It is notably preferred, although not required, that the zirconia-containing support be substantially free of silica, tungsten oxide and sulfate dopants. As the term is used herein, "substantially free" means that there is less than 0.05 mol % of any combination of these three dopant materials, in total, based on moles of zirconia. Preferably there is less than 0.01 mol % on the same basis. As the term is used herein, "dopant" means impurities or intentionally added compounds that are present in very small amounts but affect certain properties of a material, often by altering the crystal structure in some way. In the present case "dopant" also means that the material is included as a part of the support and not as part of the catalytic material that is dispersed on and/or, in the case of porous supports, in the pores of the support. However, sulfate promoters may be present as part of the catalytic material, i.e., not as part of the support, at least prior to any thermal treatments that may result in some degree of migration. When present as such promoters, they are preferable in an amount ranging from 0.1 mole percent to 5 mole percent, based on the moles of the iron.

It is also, in certain non-limiting embodiments, within the scope of the invention to include at least one additional metal, in either free or combined form, as a promoter to the iron. Such may be selected from alkali metals and alkaline earth metals and combinations thereof, but alkali metals are particularly preferred. Particular examples may include, in non-limiting embodiments, lithium (Li), sodium (Na), potassium (K), rubidium (Rb), cesium (Cs), magnesium (Mg), calcium (Ca), strontium (Sr), barium (Ba), and combinations thereof. Of these, sodium, potassium, cesium and combinations thereof may be particularly preferred. Generally the source of such promoter metal is desirably a corresponding salt that can be incorporated in or on the catalyst precursor composition at any stage of the catalyst precursor composition's preparation, including in conjunction with dispersal of the iron-containing compound in or on the support.

In general it is preferred that the iron be present in the catalyst precursor compound in a range from 1 wt % to 20 wt %, based on the combined weight of the iron and the support; more preferably from 1 wt % to 15 wt %; and most preferably from 4 wt % to 10 wt %. It is also preferred that the yttria content range from 0.1 mol % to 95 mol %, and in some embodiments from 1 mol % to 75 mol %, preferably from 1 mol % to 40 mol %, and more preferably from 1 mol % to 20 mol %, based on combined moles of yttria and zirconia. Finally, if an alkali metal, alkaline earth metal, or combination thereof is included, it is preferably present in an amount from greater than 0 mol % up to 6 mol %; more preferably from 1 to 4 mol %; and most preferably from 2 mol % to 4 mol %, based upon moles of iron.

Once the catalyst precursor materials are assembled and calcined as previously described, it is desirable to carry out some kind of treatment to "activate" the catalyst. This activation process frequently includes some form of a carburization in carbon monoxide (CO), which operates to convert at least a portion of the iron oxides that result from thermal decomposition of the iron-containing starting material to form iron carbides, which are recognized to be the active catalytic agents of iron-based catalysts. Those skilled in the art will be aware of a variety of treatments to accomplish this. See, for example, EP 2 314 557 A1; WO 2009 02222 A2; WO 2008 009076 A1; Luo et al., "Fischer-Tropsch synthesis catalyst activation of low alpha iron catalyst" *Catalysis Today,* 140, 127 (2009); Shroff, et al., "Activation of Precipitated Iron Fischer-Tropsch Synthesis Catalysts," *J. Catal.,* 156 (1995), 185-207; and Bian, et al., "Studies with Precipitated Iron Fisher-Tropsch Catalyst Reduced by $H_2$ or CO," *J. of Mol. Catal. A: Chemical,* 186, (2002), 203-213; all of which are incorporated herein by reference in their entireties.

The catalysts of the present invention may be particularly useful in typical FT conversions of synthesis gas to form light olefins. Such may be deployed in typical fixed bed-type apparatus through which the synthesis gas is flowed. The synthesis gas may, in certain embodiments, include a proportion of carbon dioxide ($CO_2$) as well as the defining constituency of carbon monoxide (CO) and hydrogen ($H_2$). In certain particular embodiments the synthesis gas includes a $H_2$:CO ratio ranging from 0.5 to 3, preferably from 0.5 to 1.5, and more preferably from 0.5 to 1, and a purity of at least 90 vol %, more preferably at least 95 vol %. The remainder of the feedstock gas may be inert gases such as nitrogen, noble gases, or combinations thereof. Preferably the level of $CO_2$ is less than 50 vol %, and more preferably may range from 0 vol % to 10 vol %. Those skilled in the art will be very familiar with means and methods of running such conversion reactions on a variety of scales ranging from laboratory scale to large-scale commercial production and will easily understand and envision, without further direction, variations of typical parameters in order to accomplish desired production goals.

EXAMPLES

Examples 1-7 and Comparative Examples 1-7

A series of catalyst precursor compositions is prepared as described. A solution containing the desired amounts of iron and alkali metals is prepared for each of Examples 1-4 and Comparative Examples 1-7, containing the constituents shown in Table 1, by dissolving the precursor salts in deionized water. Each catalyst precursor is then prepared by incipient wetness impregnation of the solution on the designated support. Each catalyst precursor is dried at 120° C. The impregnation and drying steps are repeated until all the solution has been loaded onto the supports in order to obtain the desired iron content (wt %). The resulting catalyst precursor compositions are each calcined in air at 500° C. for 4 hours (h).
Test in FTO Conditions All catalyst precursor compositions are then treated for activation and then tested in a Fischer-Tropsch-to-olefins (FTO) reaction following the same methodology. For all Examples and Comparative Examples, except for Examples 5, 6, and 7, a fixed volume of 100 microliters (μL) of catalyst is mixed with silicon carbide and loaded in a tubular reactor. For Examples 5, 6, and 7, 25 milligrams (mg) of catalyst is mixed with silicon carbide and loaded to a tubular reactor. The reactor is heated to 425° C. and pressurized to 0.3 MPa. After stabilization, a reduction step is initiated by flowing a stream of 5 milliliters per minute (mL/min) of hydrogen ($H_2$) for 3 h.

After that, the $H_2$ flow is stopped and replaced by a flow of nitrogen ($N_2$). The reactor temperature is cooled down to 340° C., the pressure is raised to 2 MPa, and a 5 mL flow consisting of 45 vol % CO, 45 vol % $H_2$, and 10 vol % $N_2$ is introduced. The reaction is left to proceed at these conditions for 60 h. Data used for comparison are taken after a minimum of 10 h in order to allow the system to stabilize. Special care is taken to compare data obtained for different catalyst at approximately the same conversion percent, i.e., within 2 percent of each other, as shown in Table 1 (Note: Table 1 has been broken into sub-tables, denominated Tables 1.1 through 1.6, in order to more easily illustrate comparisons.)

Example 1

A commercially available yttria/zirconia containing 10 mol % $Y_2O3$ (TOSOH™ TZ-10YS; TOSOH™ is a tradename of Tosoh Corporation) is selected as the support. A solution is prepared by dissolving the desired amount of an ammonium iron citrate precursor (Sigma-Aldrich, 16.2 wt % Fe) to achieve the desired iron concentration of 1.4 moles per liter (mol/L). The desired amount of potassium nitrate (Sigma-Aldrich) is also dissolved to achieve a Fe/K molar ratio of 20. The resulting solution is impregnated onto the support by incipient wetness impregnation until the solid support is filled with liquid. Then the sample is dried in an oven at 120° C. for 1 hour (h), and the impregnation/drying sequence is repeated until all the solution is impregnated onto the support. Finally, the support is calcined at 500° C. for 4 h.

The test in FTO reaction is performed as described in the section "Test in FTO conditions." The results are summarized in Table 1.

Example 2

A catalyst precursor is prepared as in Example 1, but using a different commercially available yttria/zirconia support, TOSOH™ TZ-4YS which has 4 mol % $Y_2O_3$. No potassium nitrate is used. All other processing, testing, and results recording is the same as in Example 1.

Example 3

A catalyst precursor is prepared as in Example 1, but using as the yttria/zirconia support TOSOH™ TZ-4YS, containing 4 mol % $Y_2O_3$. The desired amount of cesium sulfate ($Cs_2SO_4$, Sigma-Aldrich) is also dissolved to achieve a Fe/Cs molar ratio of 125. All other processing, testing, and results recording are the same as in Example 1.

Example 4

A catalyst precursor is prepared as in Example 3, but using TOSOH™ TZ-10YS, containing 10 mol % $Y_2O_3$. Both ammonium iron citrate precursor (Sigma-Aldrich, 16.2 wt % Fe), to achieve the desired iron concentration of 1.4 mol/L, and $Cs_2SO_4$, to achieve a Fe/Cs molar ratio of 125, are dissolved to form the precursor solution. All other processing, testing, and results recording are the same as in Example 1.

Example 5

A catalyst precursor is prepared as in Example 3, but using TOSOH™ TZ-10YS, containing 10 mol % $Y_2O_3$.

Both ammonium iron citrate precursor (Sigma-Aldrich, 16.2 wt % Fe), to achieve a desired iron concentration of 1.4 mol/L, and $K_2SO_4$ and $Na_2SO_4$, to achieve a Fe/alkali molar ratio of 17 and a K/Na molar ratio of 3, are dissolved to form the precursor solution. All other processing, testing, and results recording are the same as in Example 1.

Example 6

A catalyst precursor is prepared as in Example 3, but using TOSOH™ TZ-10YS, containing 10 mol % $Y_2O_3$. Both ammonium iron citrate precursor (Sigma-Aldrich, 16.2 wt % Fe), to achieve the desired iron concentration of 1.4 mol/L, and $K_2SO_4$ and $Na_2SO_4$, to achieve a Fe/alkali molar ratio of 17 and a K/Na molar ratio of 3, are dissolved to form the precursor solution. All other processing, testing, and results recording are the same as in Example 1.

Example 7

A catalyst precursor is prepared as in Example 3, but using TOSOH™ TZ-10YS, containing 10 mol % $Y_2O_3$. Both ammonium iron citrate precursor (Sigma-Aldrich, 16.2 wt % Fe), to achieve the desired iron concentration of 1.4 mol/L, and $K_2SO_4$, $Na_2SO_4$ and $Rb_2SO_4$, to achieve a Fe/alkali molar ratio of 17 and a K/Na/Rb molar ratio of 1/3.25/0.75, are dissolved to form the precursor solution. All other processing, testing, and results recording are the same as in Example 1.

Example 8

A catalyst precursor is prepared as in Example 1, but using TOSOH™ TZ-18YS, which contains 18 mol % $Y_2O_3$, as the support. The solution contains the ammonium iron citrate precursor and also potassium nitrate (Sigma-Aldrich) to achieve a Fe/K molar ratio of 125. No $Cs_2SO_4$ is included. All other processing, testing, and results recording are the same as in Example 1.

Example 9

An yttria/zirconia support containing 74 mol % $Y_2O_3$ is prepared as follows. A solution containing 0.6 mol/L of yttrium is prepared by dissolving the desired amounts of yttrium nitrate hexahydrate (Sigma-Aldrich) into demineralized water. Another solution containing 0.49 mol/L of zirconium is obtained by dissolving the desired amount of zirconyl nitrate hydrate in demineralized water. The two solutions are co-precipitated by adding dropwise the desired amounts of each solution to an excess ammonia solution (2 mol/L) to achieve the final molar ratio. After aging 3 h at 70° C., the precipitate is filtered and washed several times with demineralized water. The resulting solid is dried in an oven overnight at 120° C. and finally calcined at 1200° C. for 4 h resulting in the yttria/zirconia material serving as support.

A solution is then prepared by dissolving the desired amount of an ammonium iron citrate precursor (Sigma-Aldrich, 16.2 wt % Fe) to achieve the desired iron concentration of 1.4 mol/L. The desired amount of potassium sulfate (Sigma-Aldrich) is also dissolved to achieve a Fe/K molar ratio of 50. The resulting solution is impregnated onto the support by incipient wetness impregnation until the solid support is filled with liquid. Then the sample is dried in an oven at 120° C. for 1 h, and the impregnation/-drying sequence is repeated until all the solution is impregnated onto the support to achieve a final loading of 5 wt % Fe based on combined weights of iron and the support. Finally, the catalyst precursor is obtained by calcination at 500° C. for 4 h. The Test in FTO Conditions is performed as described hereinabove and results are summarized in Table 1.

Example 10

The commercially available yttria/zirconia support containing 10 mol % $Y_2O_3$ (TOSOH™ TZ-10YS) is selected as the support. A solution is prepared by dissolving the desired amount of an ammonium iron citrate precursor (Sigma-Aldrich, 16.2 wt % Fe) to achieve the desired iron concentration of 1.4 mol/L. The desired amounts of potassium sulfate and potassium nitrate (Sigma-Aldrich) are also dissolved to achieve a Fe/K molar ratio of 50, so that an equimolar amount of potassium is introduced from each precursor. Subsequent processing is then carried out as in previous examples, with the impregnation/drying sequence being repeated until all solution is impregnated onto the support to achieve a final loading of 5 wt % Fe based on combined weights of iron and the support. Calcination, testing, and results recording also are as carried out for previous examples.

Comparative Example 1

This comparative example is the same as Example 1 except that the support is a commercially available zirconia without yttria (TOSOH™ TZ-0).

Comparative Example 2

This comparative example is the same as Example 2 except that the support is the same as in Comparative Example 1, i.e., TOSOH™ TZ-0.

Comparative Example 3

This comparative example is the same as Example 3 except that the support is the same as in Comparative Example 1, i.e., TOSOH™ TZ-0.

Comparative Example 4

This comparative example is the same as Example 4 except that the support is the same as in Comparative Example 1, i.e., TOSOH™ TZ-0.

Comparative Example 5

This comparative example is the same as Example 9 except that the support is the same as in Comparative Example 1, i.e., TOSOH™ TZ-0.

Comparative Example 6

This comparative example is the same as Example 1 except that the support is a commercially available sulfated zirconia (NORPRO™ SZ61192; NORPRO™ is a tradename of Saint-Gobain NorPro Corporation) having a sulfur content of 4.7 wt %. The support is impregnated by a solution containing a mixture of ammonium iron citrate and potassium sulfate having a Fe/K molar ratio of 50 to achieve an iron loading of 5 wt % based on combined weights of iron and support. All other synthesis steps are the same as described in Example 1. The FT test is performed under the same conditions as described in Example 1, but this catalyst displays a very low activity with less than 5% CO conversion, indicating that a sulfate/zirconia support is not desirable for use with iron to prepare a catalyst that is active in the production of light olefins from synthesis gas.

Comparative Example 7

An all-yttria support is prepared as follows. A solution containing 0.6 mol/L of yttrium is prepared by dissolving the desired amounts of yttrium nitrate hexahydrate (Sigma-Aldrich) into demineralized water. The solution is precipitated by adding it dropwise to an excess ammonia solution (2 mol/L). After aging 3 h at 70° C., the precipitate is filtered and washed several times with demineralized water. The resulting solid is dried in an oven overnight at 120° C. and finally calcined at 1200° C. for 4 h resulting in the yttria material serving as support. A solution is prepared by dissolving the desired amount of an ammonium iron citrate precursor (Sigma-Aldrich, 16.2 wt % Fe) to achieve the desired iron concentration of 1.4 mol/L. The desired amounts of potassium sulfate and potassium nitrate (Sigma-Aldrich) are also dissolved to achieve a Fe/K molar ratio of 50, so that an equimolar amount of potassium is introduced from each precursor. The resulting solution is impregnated onto the support by incipient wetness impregnation until the solid support is filled with liquid. Then the sample is dried in an oven at 120° C. for 1 h, and the impregnation/drying sequence is repeated until all the solution is impregnated onto the support to achieve a final loading of 5 wt % Fe based on combined weights of iron and the support. Finally, the catalyst precursor is obtained by calcination at 500° C. for 4 h. Testing and recording of results are carried out as in previous examples and comparative examples.

TABLE 1

Table 1.1

| | Yttria content (mol %) | Fe content (wt %) | Promoter salt | Alkali content % mol/molFe | Conversion (%) | C2 O/(O + P) (%) | C3 O/(O + P) (%) |
|---|---|---|---|---|---|---|---|
| C. Ex. 1 | 0 | 5 | KNO$_3$ | 5 | 70 | 41 | 85 |
| Ex. 1 | 10 | 5 | KNO$_3$ | 5 | 71 | 57 | 89 |

Table 1.2

| | Yttria content (mol %) | Fe content (wt %) | Promoter salt | Alkali content | Conversion (%) | C2 O/(O + P) (%) | C3 O/(O + P) (%) |
|---|---|---|---|---|---|---|---|
| C. Ex. 2 | 0 | 5 | NA | NA | 51 | 23 | 71 |
| Ex. 2 | 4 | 5 | NA | NA | 52 | 31 | 77 |

Table 1.3

| | Yttria content (mol %) | Fe content (wt %) | Promoter salt | Alkali content % mol/molFe | Conversion (%) | C2 O/(O + P) (%) | C3 O/(O + P) (%) |
|---|---|---|---|---|---|---|---|
| C. Ex. 3 | 0 | 5 | Cs$_2$SO$_4$ | 0.8 | 89 | 13 | 59 |
| Ex. 3 | 4 | 5 | Cs$_2$SO$_4$ | 0.8 | 89 | 23 | 74 |
| Ex. 4 | 10 | 5 | Cs$_2$SO$_4$ | 0.8 | 88 | 30 | 80 |
| Ex. 5 | 10 | 10 | K$_2$SO$_4$ + Na$_2$SO$_4$ | 6 (4.5 + 1.5) | 87 | 32 | 82 |
| Ex. 6 | 10 | 10 | K$_2$SO$_4$ + Na$_2$SO$_4$ | 6 (4.5 + 1.5) | 88 | 42 | 85 |
| Ex. 7 | 10 | 15 | K$_2$SO$_4$ + Na$_2$SO$_4$ + Rb$_2$SO$_4$ | 6 (3.9 + 1.2 + 0.9) | 89 | 43 | 85 |

Table 1.4

| | Yttria content (mol %) | Fe content (wt %) | Promoter salt | Alkali content % mol/molFe | Conversion (%) | C2 O/(O + P) (%) | C3 O/(O + P) (%) |
|---|---|---|---|---|---|---|---|
| C. Ex. 4 | 0 | 5 | KNO$_3$ | 2 | 50 | 23 | 70 |
| Ex. 8 | 18 | 5 | KNO$_3$ | 2 | 50 | 50 | 86 |

Table 1.5

| | Yttria content (mol %) | Fe content (wt %) | Promoter salt | Alkali content % mol/molFe | Conversion (%) | C2 O/(O + P) (%) | C3 O/(O + P) (%) |
|---|---|---|---|---|---|---|---|
| C. Ex. 5 | 0 | 5 | K$_2$SO$_4$ | 2 | 25 | 50 | 84 |
| Ex. 9 | 74 | 5 | K$_2$SO$_4$ | 2 | 25 | 65 | 90 |
| C. Ex. 6 | 0 | 5 | K$_2$SO$_4$ | 2 | 5* | — | — |

TABLE 1-continued

Table 1.6

| | Yttria content (mol %) | Fe content (wt %) | Promoter salt | Alkali content % mol/molFe | Conversion (%) | C2 O/(O + P) (%) | C3 O/(O + P) (%) |
|---|---|---|---|---|---|---|---|
| Ex. 10 | 10 | 5 | $K_2SO_4$ + $KNO_3$ | 2 (1 + 1) | 26 | 64 | 92 |
| C. Ex. 7 | 100 | 5 | $K_2SO_4$ + $KNO_3$ | 2 (1 + 1) | 25 | 52 | 86 |

O/(O + P) means percentage of the named (C2 or C3) olefin per combined percentage of all olefins and paraffins.
*indicates poor suitability of the 4.7 wt % sulfur-containing support with iron.
— indicates no data obtained.

The invention claimed is:

1. A catalyst comprising
an iron compound comprising iron carbides and, optionally, an alkali metal, alkaline earth metal, or a combination thereof,
on a support comprising zirconia and yttria,
the iron being present in an amount ranging from 1 weight percent to 20 weight percent, based on combined weight of the iron and the support;
the yttria being present in an amount ranging from 1 mole percent to 95 mole percent, based on combined moles of yttria and zirconia, and
the optional alkali metal, alkaline earth metal or combination thereof being present in an amount ranging from 0 mole percent to 6 mole percent, based on moles of the iron.

2. The catalyst of claim 1, wherein the support is substantially free of silica, tungsten oxide and sulfate dopants.

3. The catalyst of claim 1 further comprising a sulfate promoter on the support in an amount ranging from 0.1 mole percent to 5 mole percent, based on the moles of the iron.

4. The catalyst of claim 1 wherein the yttria is present in an amount ranging from 1 mole percent to 75 mole percent, based on combined moles of the yttria and zirconia.

5. The catalyst of claim 1 wherein the yttria is present in an amount ranging from 1 mole percent to 20 mole percent, based on combined moles of the yttria and zirconia.

6. A process for converting synthesis gas to olefins, comprising contacting synthesis gas and the catalyst of claim 1 under reaction conditions sufficient to convert, at a selected carbon monoxide conversion percentage, at least a portion of the synthesis gas to a mixture of hydrocarbons that has an ethylene content and a propylene content, each of the ethylene content and the propylene content being greater than the ethylene content and the propylene content resulting from use of an otherwise identical catalyst that is substantially free of yttria, under otherwise identical reaction conditions and at a carbon monoxide conversion percent that is within 2 percent of the selected carbon monoxide conversion percent.

7. The process of claim 6, wherein the ethylene and propylene contents resulting from use of the catalyst of claim 1 are, respectively, at least 20 percent greater and at least 4 percent greater than the ethylene content and the propylene content resulting from use of the otherwise identical catalyst.

8. A catalyst prepared by a process comprising
(1) dispersing an iron-containing compound and, optionally, an alkali metal, an alkaline earth metal, or a combination thereof, on a particulate catalyst support comprising zirconia and yttria;
the amount of the iron-containing compound ranging from 1 weight percent to 20 weight percent, based on combined weight of the iron and the support;
the amount of the optional alkali metal, alkaline earth metal, or combination thereof ranging from 0 mole percent to 6 mole percent, based on combined moles of the alkali metal, the alkaline earth metal, or combination thereof and the iron; and
the amount of yttria ranging from 0.1 mole percent to 95 mole percent, based on combined moles of yttria and zirconia;
(2) thermally at least partially decomposing the iron-containing compound to form a catalyst precursor composition comprising an iron oxide;
(3) subjecting the catalyst precursor composition to at least partial carburization in a carbon monoxide-containing atmosphere to convert at least some of the iron oxides to iron carbides.

9. The catalyst prepared by the process of claim 8, wherein the iron-containing compound comprises Fe(II), Fe(III) or both.

10. The catalyst of claim 1, wherein the iron compound is in amounts from 4 weight percent to 15 weight percent, based on combined weight of the iron and the support.

11. The catalyst of claim 10, wherein the support is substantially free of silica and tungsten oxide.

12. The catalyst of claim 10, wherein the yttria is present in an amount ranging from 1 mole percent to 75 mole percent, based on combined moles of the yttria and zirconia.

13. The catalyst of claim 10, wherein the yttria is present in an amount ranging from 1 mole percent to 20 mole percent, based on combined moles of the yttria and zirconia.

14. A catalyst comprising:
iron, a sulfate promoter, and optionally, an alkali metal, alkaline earth metal, or a combination thereof,
on a support comprising zirconia and yttria,
the iron being present in an amount ranging from 1 weight percent to 20 weight percent, based on combined weight of the iron and the support;
the sulfate promoter being present in an amount ranging from 0.1 mole percent to 5 mole percent, based on the moles of the iron;
the yttria being present in an amount ranging from 1 mole percent to 95 mole percent, based on combined moles of yttria and zirconia; and
the optional alkali metal, alkaline earth metal or combination thereof being present in an amount ranging from 0 mole percent to 6 mole percent, based on moles of the iron.

* * * * *